United States Patent [19]

Mori et al.

[11] Patent Number: 5,244,803
[45] Date of Patent: Sep. 14, 1993

[54] PROCESS FOR PREPARING OPTICALLY ACTIVE 3-PHENYLGLYCIDIC ACID ESTERS

[75] Inventors: Takao Mori, Takatsuki; Toshiyuki Furutani; Akio Nakao, both of Osaka; Atsuhiko Tsujimura, Takatsuki; Takeji Shibatani, Kobe, all of Japan

[73] Assignee: Tanabe Seiyaku Co., Ltd., Osaka, Japan

[21] Appl. No.: 578,904

[22] Filed: Sep. 7, 1990

[30] Foreign Application Priority Data

Sep. 13, 1989 [JP] Japan .................. 1-237738

[51] Int. Cl.$^5$ .......................... C07D 281/02
[52] U.S. Cl. .................. 435/280; 435/123; 435/824; 435/832; 435/840; 435/843; 435/850; 435/859; 435/863; 435/874; 435/878; 435/910; 435/921; 435/938; 540/491
[58] Field of Search .................. 435/280, 123

[56] References Cited

U.S. PATENT DOCUMENTS

| | | | |
|---|---|---|---|
| 4,567,175 | 1/1986 | Takeda et al. | 514/211 |
| 4,590,188 | 5/1986 | Takeda et al. | 514/211 |
| 4,898,822 | 2/1990 | Asada et al. | |
| 4,923,810 | 5/1990 | Walts et al. | 435/117 |

FOREIGN PATENT DOCUMENTS

| | | | |
|---|---|---|---|
| 62433 | 3/1987 | Australia . | |
| 158339 | 4/1985 | European Pat. Off. . | |
| 237983 | 3/1987 | European Pat. Off. . | |
| 237080 | 9/1987 | European Pat. Off. | 435/123 |
| 0264457 | 4/1988 | European Pat. Off. . | |
| 325954 | 8/1989 | European Pat. Off. . | |
| 333142 | 9/1989 | European Pat. Off. | 435/123 |
| 343714 | 11/1989 | European Pat. Off. | 435/123 |
| 362556 | 4/1990 | European Pat. Off. | 435/123 |
| 90/643 | 5/1990 | World Int. Prop. O. | 435/123 |

OTHER PUBLICATIONS

Tetrahedron, vol. 41, No. 7, (1985) pp. 1393-1399, Pergamon Press Ltd., GB; P. Melloni et al.: "Configurational studies on 2-[alpha-(2-ethoxyphenoxy)benzyl]-morpholine FCE 20124" *Whole document*.

Philippi, M. Chr. et al., "Enantioselective Hydrolysis and Transesterification of Glycidyl Butyrate by Lipase Preparations from Porcine Pancreas",: in *Biocatalysis in Organic Media*, C. Laane et al., (Ed.), Proceedings of an International Symposium held at Wageningen, The Netherlands, Dec. 7-10, 1986.

Ladner, W. E., et al., "Lipase-Catalyzed Hydrolysis as a Route to Esters of Chiral Epoxy Alcohols," *J. Am. Chem. Soc.* 106:7250-7251 (1986).

Schneider, M. et al "Enzymatic Syntheses of Chiral Building Blocks from Racemates: Preparation of (1R,3R)-Chrysantemic-Permethrinic and —Casonic Acids from Racemic Diastereomeric Mixtures," *Angew. Chem. Int. Ed. Engl.* 23(1):64-66 (1984).

Schneider, M. et al., "Enzymatic Synthesis of Chiral Building Blocks from Prochiral Substrates: Enantioselective Synthesis of Monoalkyl Malonates," *Angew. Chem., Int. Ed. Engl.* 23(1):66 (1984).

Melloni, P. et al. "Configurational Studies of 2-[α-(2-ethoxyphenoxy)Benzyl]Morpholine FCE 20123," *Tetrahedron* 41(7):1393-1399 (1985).

"Optically active 3-(p-methoxyphenyl)glcycidic acid derivatives," *Chemical Abstracts* 103:7119w, p. 638 (1985).

"Optically active potassium 3-(p-methoxyphenyl)=-glycidate," *Chemical Abstracts* 103:71180q, p. 638 (1985).

*Primary Examiner*—Allen J. Robinson
*Attorney, Agent, or Firm*—Browdy and Neimark

[57] ABSTRACT

There is disclosed a process for preparing optically active 3-phenylglycidic acid ester compound, which comprises permitting a culture broth, cells or treated cells of a microorganism having an ability of stereoselectively hydrolyzing a (2R, 3S)-3-phenylglycidic acid ester compound to act on a racemic 3-phenylglycidic acid ester compound which may also have a substituent on the phenyl group, thereby hydrolyzing the (2R, 3S) optically active isomer and separating and collecting the (2S, 3R) antipode from the reaction mixture.

8 Claims, 3 Drawing Sheets

PROCESS FOR PREPARING OPTICALLY ACTIVE 3-PHENYLGLYCIDIC ACID ESTERS

BACKGROUND OF THE INVENTION

This invention relates to a novel process for preparing (2S, 3R)-3-phenylglycidic acid esters.

(2S, 3R)-3-phenylglycidic acid esters are important compounds as synthetic intermediates of 1,5-benzothiazepine derivatives (U.S. Pat. No. 4,590,188) having coronary blood vessel vasodilating activity or platelet aggregation-inhibiting activity, and other various pharmaceutical compounds. In the prior art, as the method for preparing such a (2S, 3R) type compound, there has been known the method in which a racemic mixture of methyl trans-3-(4methoxyphenyl)glycidate is hydrolyzed to form a corresponding carboxylic acid, which carboxylic acid is optically resolved with an optically active amine and then esterified to give methyl (2S, 3R)-3-(4-methoxyphenyl)glycidate (Chemical Abstract, 103, 71179w and 71180q (1985)).

However, the above-mentioned method has many steps, and also there was involved the drawback that the product of the optically active methyl 3-(4-methoxyphenyl)glycidate could be obtained only as an oily product with low purity.

SUMMARY OF THE INVENTION

The present inventors have studied intensively in order to solve such drawbacks, and consequently found that microorganisms of the genus Micrococcus have an ability of stereoselectively hydrolyzing specifically (2R, 3S)-3-phenylglycidic acid ester compounds, to accomplish the present invention.

More specifically, according to the present invention, there is provided a process for preparing an optically active (2S, 3R)-3-phenylglycidic acid ester compound which comprises (a) permitting a culture broth, cells or treated cells of a microorganism having the ability of stereoselectively hydrolyzing a (2R, 3S)-3-phneylglycidic acid ester compound to act on a racemic 3-phenylglycidic acid ester compound represented by the formula:

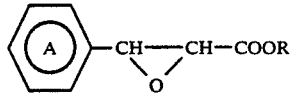

(I)

wherein Ring A is a substituted or unsubstituted phenyl group, and R is an ester residue, thereby stereoselectively hydrolyzing (2R, 3S) optical active isomer, and then (b) separating and collecting a (2S, 3R)-3-phenylglycidic acid ester compound from a reaction mixture.

DESCRIPTION OF THE PREFERRED EMBODIMENTS

Figure 1:
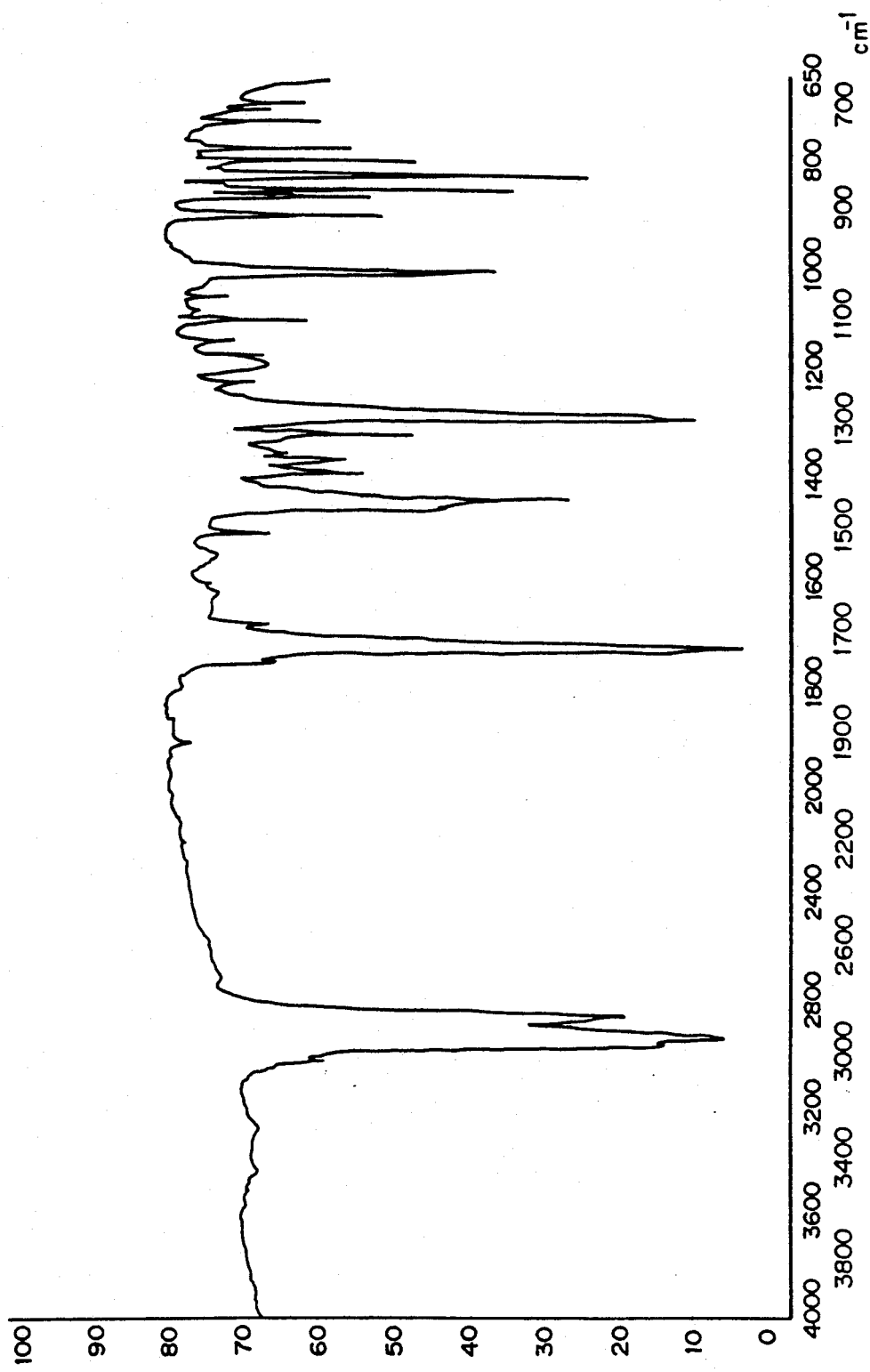
FIG. 1 is an IR absorption spectrum of methyl (2S, 3R)-3-(4-methylphenyl)glycidate.

The process of the present invention can be practiced similarly in either the case when Ring A has a substituent selected from a lower alkyl group, a lower alkoxy group and a halogen atom or not. As such a substituent, for example, there is methyl group, methoxy group or chlorine atom at the 4-position. As the ester residue R, lower alkyl groups are generally preferred, as exemplified by methyl group, ethyl group, isopropyl group or t-butyl group.

In the present invention, as the racemic 3-phenylglycidic acid ester compound (I) which is the starting material, not only one containing equal amounts of (2S, 3R) isomer and (2R, 3S) isomer, but any one containing both of these optically active isomers can be employed.

As the microorganism which can be used in the present invention, a microorganism having an ability of hydrolyzing stereoselectively a (2R, 3S)-3-phenylglycidic acid ester compound (I) may be employed. For example, microorganisms such as bacteria, yeasts, molds and actinomycetes having such ability can be suitably employed. More specifically, there may be included bacteria belonging to the genus Micrococcus, the genus Achromobacter, the genus Agrobacterium, the genus Corynebacterium, the genus Enterobacter, the genus Flavobacterium, the genus Microbacterium, the genus Pseudomonas, the genus Rhizobium, the genus Sarcina, the genus Bacillus, the genus Brevibacterium, the genus Citrobacter and the genus Xanthomonas, yeasts belonging to the genus Candida, the genus Debaryomyces, the genus Hanseniaspora, the genus Hansenula, the genus Pichia, the genus Rhodosporidium, the genus Schizosaccharomyces, the genus Sporobolomyces, the genus Torula, the genus Kloeckera, the genus Rhodotorula, the genus Saccharomycopsis, the genus Torulaspora and the genus Trigonopsis, molds belonging to the genus Absidia and the genus Aspergillus, and actimocytes belonging to the genus Streptomyces. Specific examples of such microorganisms may include, for example, *Micrococcus ureae* IAM 1010 (FERM BP-2996), *Achromobacter butyri* OUT 8004, *Achromobacter dendriticum* OUT 8009, *Achromobacter liguidum* OUT 8012, *Agrobacterium radiobacter* IAM 1526, Ditto IFO 13259, *Corynebacterium murisepticum* ATCC 21374, *Enterobacter cloacae* NCTC 9394, *Flavobacterium arborescens* IAM 1100, *Flavobacterium* sp. FERM P-6901, *Microbacterium* sp. ATCC 21376, *Pseudomonas dacunhae* IAM 1199, *Pseudomonas gelidicola* OUT 8116, *Pseudomonas fluorescens* IAM 1219, Ditto IAM 1236, *Pseudomonas taetrolens* IFO 3460 *Pseudomonas ovalis* IAM 1002, Ditto IAM 1177, *Pseudomonas putida* IAM 1512, Ditto FERM P-3505, *Rhizobium meliloti* IFO 13336, *Sarcina subflava* AHU 1485, *Bacillus subtilis* OUT 8234, *Brevibacterium helvolum* IAM 1637, *Brevibacterium imperiale* IAM 1654, *Citrobacter freundii* ATCC 8090, *Xanthomonas campestris* IAM 1671, *Candida boidinii* IFO 10240, *Candida guilliermondii* IFO 0566, *Candida boidinii* IFO 0747, *Candida rugosa* ATCC 10571, Ditto IFO 0591, *Candida succiphila* IFO 1911, *Candida tropicalis* IFO 1400, *Candida utilis* IFO 0626, Ditto IFO 1086, *Debaryomyces hansenii* var. fabryi IFO 0015, *Debaryomyces nepalensis* IFO 0039, *Hanseniaspora valbyensis* IFO 0115, *Hansenula polymorpha* IFO 1024, *Hansenula saturnus* HUT 7087, *Pichia farinose* IFO 0607, *Pichia pastoris* IFO 0948, Ditto IFO 1013, Ditto IAM 12267, *Pichia wickerhamii* IFO 1278, *Rhodosporidium toruloides* IFO 0559, *Schizosaccharomyces pombe* IFO 0358, *Sporobolomyces gracillis* IFO 1033, *Torula fermentati* HUT 7524, *Torula utilis* HUT 7526, *Kloeckera corticis* IFO 0633, *Rhodotorula minuta* OUT 6153, *Rhodotorula rubra* OUT 6158, *Torulaspora delbrueckii* IFO 0422, *Saccharomycopsis capsula-* ris IFO 0005, *Trigonopsis variabilis* IFO 0671, *Absidia glauca* var. *paradoxa* IFO 4007, *Aspergillus flavus* IFO 5839, *Aspergillus oryzae* IFO 5710, *Streptomyces griseus* subsp. *griseus* IFO 3430, Ditto IFO 3355 and *Streptomyces lavendulae* subsp. *lavendulae* IFO 3361, Ditto IFO 3145 and Ditto IFO 3146. These may be either wild strains or mutant strains, and further may be those derived from these microorganisms according to the bioengineering methods such as gene recombination and cell fusion.

As the medium for culturing the microorganism, any medium in which the above-mentioned microorganism can be grown. For example, there can be preferably used a medium containing, as carbon sources, 0.4 to 15% of saccharides such as glucose, sucrose and molasses, organic acids such as fumaric acid or citric acid or alcohols such as glycerol, and as nitrogen sources, 0.3 to 2.0% of inorganic ammonium salts such as ammonium sulfate and ammonium chloride or urea, or peptone, meat extract, corn-steep liquor, yeast extract and casein hydrolyzate. Further, if necessary, inorganic salts such as phosphate, magnesium salt, potassium salt and calcium salt, and metal ions of manganese and zinc, may be also present in appropriate amounts in the medium. When a synthetic medium is employed, if necessary, it is effective to add, for example, an amino acid such as proline and hystidine, or biotin or thiamine. Further, if necessary, 0.1 to 1.0% of a vegetable oil, a racemic 3phenylglycidic acid ester compound (I) and a surfactant can be also added as an enzyme deriving substance or a defoaming agent to enhance the enzyme activity. These media is preferably employed with adjustment of pH to 5 to 7.

Cultivation can be performed in conventional manner after inoculation of the microorganism onto the above-mentioned medium, for example, according to any of shaking culture, aeration stirring culture, stationary culture and continuous culture.

The cultural conditions may be chosen suitably depending on the kind of the medium, the cultural method, and not particularly limited, provided that the above-mentioned microorganism can grow to produce an esterase. Generally, it is desired to adjust the pH at initiation of culturing to 5 to 7, and carry out cultivation at room temperature or under heating, for example, at 20° to 40° C.

As the treated product of such microbial cells, there may be included lyophilized cells, acetone dried cells, selfdigested product of cells, extract of cells, ground cells, sonicated cells of the above-mentioned microbial cells and the culture supernatant. Further, the microbial cells or treated cells of the present invention can be also immobilized by known methods such as the polyacrylamide method, the sulfur-containing polysaccharide gel method (e.g. carrageenan gel method), the alginic acid gel method or the agar gel method, before use. Further, an enzyme obtained by purification from the extract of microbial cells by combination of known methods can be also employed.

The stereoselective hydrolysis reaction according to the present invention can be practiced by permitting the culture broth of the microorganism, the cells collected from said culture broth or the treated cells to contact with a racemic 3-phenylglycidic acid ester compound (I).

The substrate concentration may be generally 0.1 to 80% by weight, particularly preferably 20 to 80% by weight, and the reaction can proceed at normal temperature or under heating, preferably at 10° to 50° C., particularly preferably at 20° to 40° C. During the reaction, it is preferred to adjust the pH of the reaction mixture to 4 to 9, above all 5 to 7. As the reaction mixture, an aqueous solvent such as water or water-methanol mixture can be employed, but from the standpoint of stabilization of the substrate, the reaction can be also practiced in a two-phase solvent system of water or an aqueous solvent and an organic solvent. As such organic solvent, there may be included, for example, toluene, xylene, carbon tetrachloride, dichloromethane, trichloroethylene, chlorobenzene, ethyl aceate, butyl acetate, methyl isobutyl ketone, isooctane, acetone, isopropyl ether, tert-butyl methyl ether, methyl alcohol, ethyl alcohol, n-propyl alcohol, isopropyl alcohol, n-butyl alcohol and t-butyl alcohol, particularly preferably toluene, methyl isobutyl ketone, ethyl alcohol and carbon tetrachloride. Also, by practicing the above reaction in the presence of a surfactant, shortening of the reaction time and increase of yield of the (2S, 3R)-3-phenylglycidic acid ester compound (I) can be effected. As such a surfactant, there can be employed cetylpyridinium bromide, cetyltrimetylammonium bromide, polyethylene glycol and polyoxyethylene octylphenyl ether, and its amount added may be preferably about 0.0001 to 0.1% by weight based on the reaction mixture.

Isolation of the (2S, 3R)-3-phenylglycidic acid ester compound (I) thus obtained from the hydrolysis reaction mixture can be easily practiced according to the conventional method. For example, when the hydrolysis reaction is carried out in a water-organic solvent two-phase system, the (2R, 3S)-3-phenylglycidic acid ester type compound (I) is hydrolyzed to be migrated into the aqueous layer, while the (2S, 3R) optically active isomer remains in the organic solvent, and therefore by separating the organic solvent layer and concentrating it under reduced pressure, the (2S, 3R)-3-phenylglycidic acid ester compound can be collected as crystals. On the other hand, when the hydrolysis reaction is practiced in an aqueous solvent, the desired product can be obtained by extracting with an organic solvent such as toluene after the reaction, and concentrating the extract under reduced pressure.

The (2S, 3R)-3-phenylglycidic acid ester compound thus obtained can be converted into (-)-cis-2-(4'-methylphenyl)3-acetyloxy-5-[2-(dimethylamino)ethyl]-8-methyl-2,3-dihydro-1,5-benzothiazepin-4(5H)-one according to the known method as described in U.S. Pat. Nos. 4,567,175 and U.S. Pat. No. 4,590,188 the contents of which are hereby incorporated by reference.

As described above, the process of the present invention can obtain a desired (2S, 3R)-3-phenylglycidic acid ester compound in a single step and yet as crystals of high purity from a racemic 3-phenylglycidic acid ester compound, and therefore can be an industrially advantageous preparation process.

EXAMPLE 1

An amount 100 ml of a medium (pH 7) containing 0.5% of glucose, 1% of peptone, 1% of meat extract, 1.25% of yeast extract, 0.5% of sodium chloride, 0.3% of a polyalkylene glycol derivative series surfactant (trade name: Karalin, available from Sanyo Kasei Kogyo K.K.) and 0.5% of a polyoxyethylene derivative series surfactant (trade name: Tween 80, available from Atlas Powder Co., USA) was charged into a 500 ml volume shaking flask, and sterilized at 120° C. for 10 minutes. Into the medium was inoculated a platinum loop of Micrococcus ureae IAM 1010 (FERM BP-2996), and shaking culture was carried out at 30° C. for 24 hours. The above culture broth (250 ml) was concentrated by an ultra-filtration membrane (molecular weight fraction: 10,000) to 1/10 to obtain concentrated microbial cells. To the concentrated microbial cells were added 25 ml of a 1 M phosphate buffer (pH 7) and 50 ml of methanol containing 10 g of a racemic methyl 3-(4-methylphenyl)glycidate, and by carrying out the stereoselective hydrolysis reaction at 30° C. for 48 hours, methyl (2R, 3S)-3-(4-methylphenyl)glycidate was completely decomposed. After the reaction, toluene was added for extraction, and the toluene layer was separated and concentrated under reduced pressure to obtain 3.2 g of methyl (2S, 3R)-3-(4-methylphenyl)-glycidate as crude crystals. To 3.2 g of the crude crystals was added n- hexane, and the crystals were dissolved by heating and then recrystallized by cooling to obtain 2.5 g of crystals of methyl (2S, 3R)-3-(4-methylphenyl)glycidate.

Figure 2:
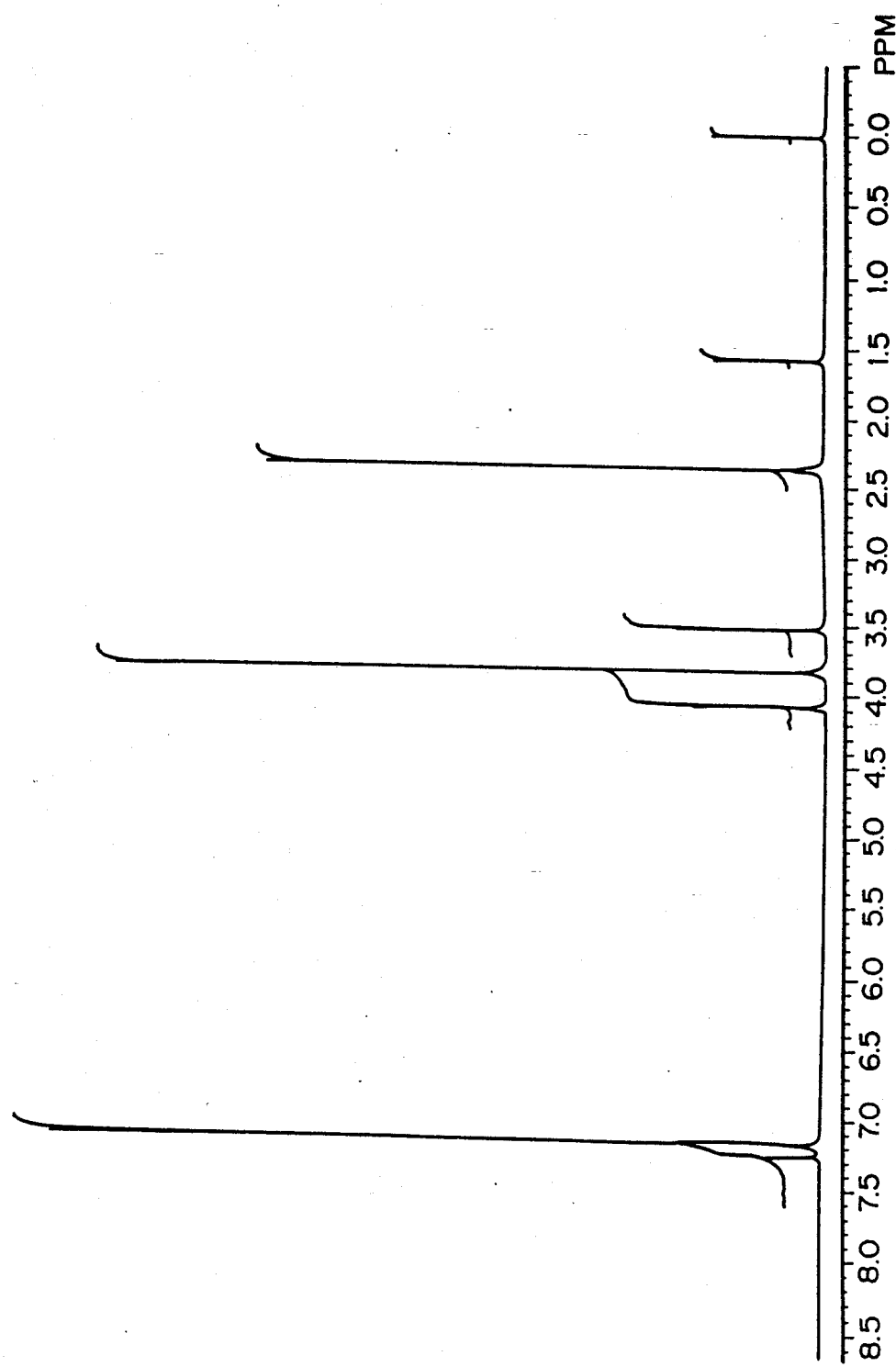
FIG. 2 is an NMR spectrum of the same compound.
Figure 3:
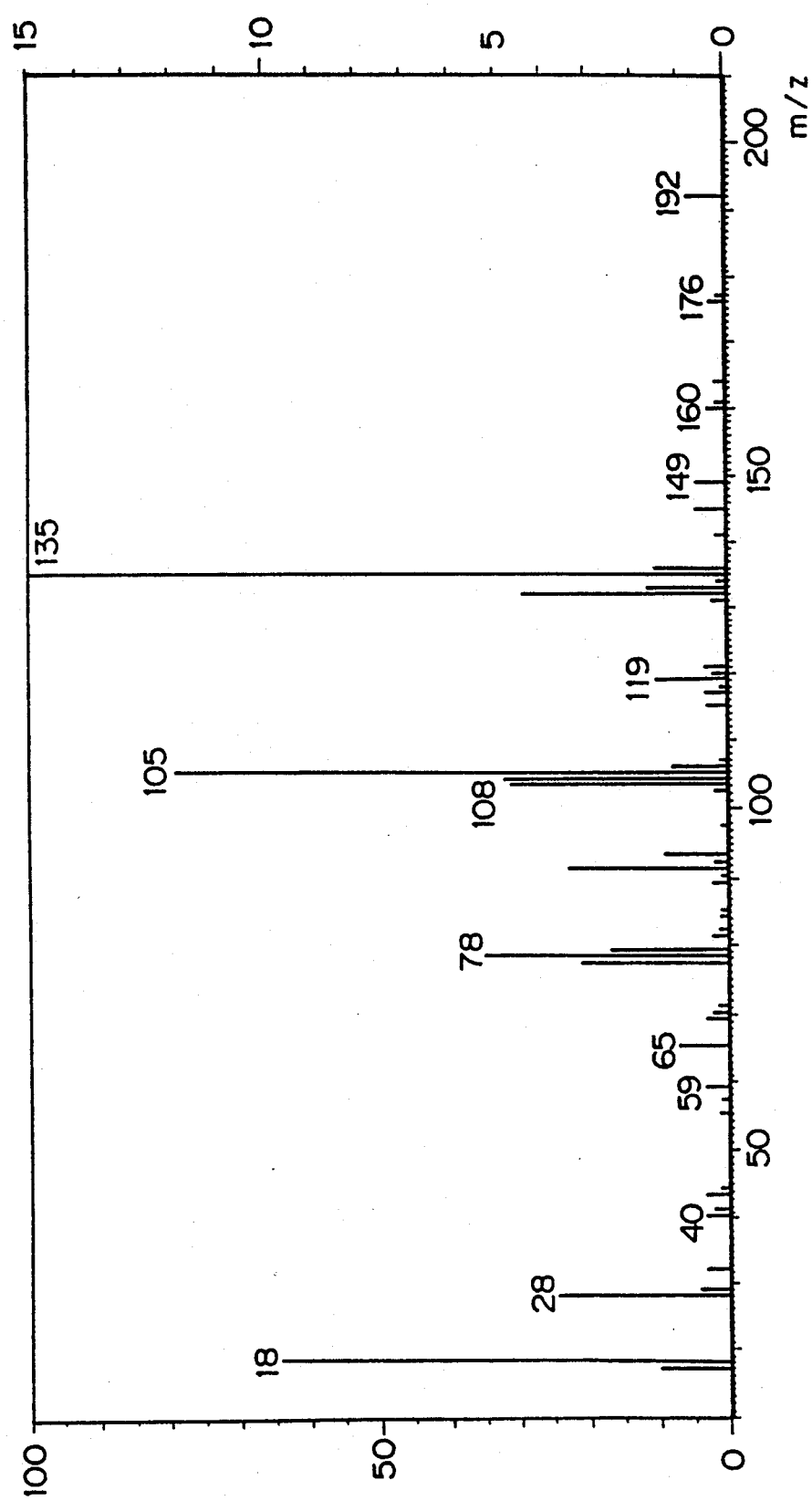
FIG. 3 is a mass analysis spectrum of the same compound.

M. P.: 50° C.
$[\alpha]_D^{20}$: +209 (C=0.2, methanol)
Optical purity: 100%
IR-absorption spectrum: FIG. 1
NMR spectrum: FIG. 2
Mass analysis spectrum: FIG. 3.

Quantitation of the above optically active isomer was performed by high performance liquid chromatography by use of a chiral cell OB Φ4.6×250 mm manufactured by Daicel Kagaku Kogyo K.K.

EXAMPLE 2

To the microbial cells collected by centrifugation from 250 ml of the culture broth obtained in the same manner as in Example 1 was added 25 ml of a 0.05 M phosphate buffer (pH and the mixture was subjected to sonication treatment and centrifugation. To the supernatant was added ammonium sulfate, and the precipitates obtained were dialyzed against a 0.05 M phosphate buffer to obtain 25 ml of a dialyzed inner solution. To the dialyzed inner solution were added 25 ml of a 0.5 M phosphate buffer (pH 7) and 25 ml of a toluene solution containing 5 g of a racemic methyl -(4-methylphenyl)-glycidate, and by carrying out the stereoselective hydrolysis reaction at 30 C. for 48 hours, methyl (2R, 3S)-3-(4-methylphenyl)glycidate was completely decomposed. The toluene layer was separated and concentrated under reduced pressure to obtain 1.5 g of methyl (2S, 3R)-3-(4-methylphenyl)glycidate. The physical constants of this product were identical with the product obtained in Example 1.

EXAMPLE 3

An amount 50 ml of a medium (pH 6.0) containing 1% of glucose, 0.5% of peptone, 0.3% of yeast extract, 0.3% of malt extract, 1% of olive oil, 0.1% of monopotassium phosphate and 1.0% of calcium carbonate was charged into a 500 ml volume shaking flask, and sterilized at 120° C. for 10 minutes. Into the medium was inoculated a platinum loop of a yeast or a mold shown below in Table 1, and the yeast was subjected to shaking culture at 27° C. for 20 hours, and the mold for 68 hours. To 45 ml of the above culture broth was added 1.5 ml of ethanol containing 60 mg of a racemic methyl 3-(4-methylphenyl)glycidate, and further cetyltrimethylammonium bromide in an amount to the final concentration in the reaction mixture of 0.01% and calcium chloride in an amount to the final concentration of 1 mM were added, and the stereoselective hydrolysis reaction was carried out at 30° C. for 20 to 68 hours. After the reaction, the substrate and the (2S, 3R) type optically active isomer which is the reaction product were extracted with 15 ml of ethyl acetate. The content of the (2S, 3R) isomer in the reaction mixture is as shown below in Table 1, and substantially no (2R, 3S) isomer which is the antipode thereof was detected in the reaction mixture.

Quantitation of the above optically active isomer was performed by high performance liquid chromatography by use of a chiral cell OJ Φ4.6×250 mm manufactured by Daicel Kagaku Kogyo K.K. (hereinafter the same).

TABLE 1

| Microorganism employed | (2S, 3R) isomer content (mg/ml) |
| --- | --- |
| Candida boidinii IFO 10240 | 1.0 |
| Candida guilliermondii IFO 0566 | 1.1 |
| Candida melinii IFO 0747 | 0.7 |
| Candida tropicalis IFO 1400 | 1.1 |
| Candida utilis IFO 0626 | 0.8 |
| Candida rugosa ATCC 10571 | 0.9 |
| Candida rugosa IFO 0591 | 0.9 |
| Candida succiphila IFO 1911 | 0.9 |
| Debaryomyces hansenii var. fabryi IFO 0015 | 1.1 |
| Debaryomyces nepalensis IFO 0039 | 1.6 |
| Hanseniaspora valbyensis IFO 0115 | 1.7 |
| Hansenula polymorpha IFO 1024 | 1.0 |
| Pichia farinosa IFO 0607 | 1.0 |
| Pichia pastoris IFO 0948 | 1.1 |
| Pichia pastoris IFO 1013 | 0.8 |
| Pichia pastoris IAM 12267 | 1.1 |
| Pichia wickerhamii IFO 1278 | 1.5 |
| Rhodosporidium toruloides IFO 0559 | 0.9 |
| Schizosaccharomyces pombe IFO 0358 | 0.8 |
| Sporobolomyces gracilis IFO 1033 | 1.6 |
| Torula fermentati HUT 7524 | 0.9 |
| Torula utilis HUT 7526 | 1.1 |
| Absidia glauca var. paradoxa IFO 4007 | 0.9 |

EXAMPLE 4

An amount 50 ml of a medium (pH 7.0) containing 0.4% of glucose, 0.4% of yeast extract, 1% of malt extract, 1% of olive oil, 0.1% of monopotassium phosphate and 1.0% of calcium carbonate was charged into a 500 ml volume shaking flask, and sterilized at 120° C. for 10 minutes. To the medium was inoculated a platinum loop of an actinomycete shown below in Table 2, and the actinomycete was subjected to shaking culture at 30° C. for 68 hours. To 45 ml of the above culture broth was added 1.5 ml of ethanol containing 60 mg of racemic methyl 3-(4-methylphenyl)glycidate, and further cetyltrimethylammonium in an amount to the final concentration of 0.01% in the reaction mixture and calcium chloride in an amount to the final concentration of 1 mM were added to carry out the stereoselective hydrolysis reaction at 30° C. for 20 to 68 hours. After the reaction, the substrate and the (2S, 3R) optically active isomer were extracted with 15 ml of ethyl acetate. The content of the (2S, 3R) isomer in the reaction mixture is as shown in Table 2, and substantially no (2R, 3S) isomer which is the antipode thereof was detected in the reaction mixture.

TABLE 2

| Microorganism employed | (2S, 3R) isomer content (mg/ml) |
| --- | --- |
| Streptomyces griseus subsp. griseus IFO 3355 | 1.8 |
| Streptomyces griseus subsp. griseus IFO 3430 | 1.6 |
| Streptomyces lavendulae subsp. lavendulae IFO 3145 | 1.4 |
| Streptomyces lavendulae subsp. lavendulae IFO 3146 | 1.4 |
| Streptomyces lavendulae subsp. lavendulae IFO 3361 | 1.3 |

EXAMPLE 5

An amount 50 ml of a medium A (pH 7.0) containing 1% of a soluble starch, 0.5% of peptone, 0.5% of yeast extract, 1 of olive oil and 0.1% of monopotassium phosphate was charged into a 500 ml volume shaking flask, and sterilized at 120° C. for 10 minutes. Into the medium A or into 50 ml of a medium B in which 1.5 ml of ethanol containing 60 mg of a racemic methyl 3-(4-methylphenyl)glycidate added to the medium A was inoculated a platinum loop of a bacterium shown below in Table 3, and subjected to shaking culture at 30° C. for 20 hours. Into 45 ml of the above culture broth A was added 1.5 ml of ethanol containing 60 mg of a racemic methyl 3-(4-methylphenyl)glycidate. To the media A and B were added cetyltrimethylammonium bromide in an amount to the final concentration of 0.01% in the reaction mixture and calcium chloride in an amount to the final concentration of 1 mM, and the stereoselective hydrolysis reaction was carried out at 30° C. for 20 to 68 hours. After the reaction, the substrate and the optically active (2S, 3R) isomer which is the reaction product were extracted with 15 ml of ethyl acetate. The content of the (2S, 3R) isomer in the reaction mixture is as shown below in Table 3, and substantially no (2R, 3S) isomer which is the antipode thereof was detected.

TABLE 3

| Microorganism employed | (2S, 3R) isomer content (mg/ml) |
| --- | --- |
| Achromobacter butiri OUT 8004 | 1.3 |
| Achromobacter dendriticum OUT 8009 | 1.0 |
| Agrobacterium radiobacter IAM 1526 | 1.2 |
| Agrobacterium radiobacter IFO 13259 | 0.8 |
| Corynebacterium murisepticum ATCC 21374 | 1.3 (Medium B) |
| Enterobater cloacae NCTC 9394 | 1.5 |
| Flavobacterium arborescens IAM 1100 | 1.0 (Medium B) |
| Microbacterium sp. ATCC 21376 | 1.0 |

TABLE 3-continued

| Microorganism employed | (2S, 3R) isomer content (mg/ml) |
| --- | --- |
| Micrococcus ureae IAM 1010 (FERM BP-2996) | 1.0 |
| Pseudomonas gelidicola OUT 8116 | 1.1 |
| Rhizobium meliloti IFO 13336 | 0.8 |
| Sarcina subflava AHU 1485 | 0.9 |

EXAMPLE 6

An amount 50 ml of medium (pH 7.0) containing 0.5% of glucose, 1% of peptone, 1% of meat extract, 1.25% of yeast extract, 0.1% of monopotassium phosphate, 0.5% sodium chloride and 1% of olive oil was charged into a 500 ml volume shaking flask, and sterilized at 120° C. for 10 minutes. Into the medium, one platinum loop of Micrococcus ureae IAM 1010 (FERM BP-2996) was inoculated, and cultivation was performed under shaking at 30° C. for 20 hours. 3.75 ml of McIlvaine buffer (pH 5.0) and 7.5 ml of organic solvent shown in Table 4 containing 30 mg of racemic methyl 3-(4-methylphenyl)glycidate were added into 3.75 ml of the above microbial cells solution concentrated ten-fold by treating with an ultrafiltration membrane (cutoff molecular weight: 10,000). Then, the stereoselective hydrolysis reaction was carried out at 30° C. for 20 hours in emulsion state. After the reaction, the organic solvent layer was separated to obtain a reaction mixture containing the (2S, 3R) isomer. The content of the (2S, 3R) isomer in the reaction mixture was shown in Table 4, and substantially no (2R, 3S) isomer which is its antipode was detected in the reaction mixture.

TABLE 4

| Solvent | (2S, 3R) isomer content (mg/ml) |
| --- | --- |
| Carbon tetrachloride | 1.8 |
| Toluene | 1.8 |
| n-Butyl acetate | 1.1 |
| p-Xylene | 1.1 |
| Methyl isobutyl ketone | 1.6 |
| Isooctane | 0.7 |
| Acetone | 0.8 |
| Ethyl alcohol | 1.5 |
| Tert-Butyl methyl ether | 0.2 |

EXAMPLE 7

An amount 50 ml of a medium (pH 7.0) containing 0.5% of glucose, 1% of peptone, 1% of meat extract, 1.25% of yeast extract, 0.5% of sodium chloride, 0.03% of a polyalkylene glycol derivative series surfactant (trade name: Karalin, available from Sanyo Kasei Kogyo K.K.), 0.1% of a polyoxyethylene derivative series surfactant (trade name: Tween 80, available from Atlas Powder Co., USA) was charged into a 500 ml volume shaking flask, and sterilized at 120° C. for 10 minutes. Into the medium was inoculated a bacterium shown below in Table 5, and subjected to shaking culture at 30° C. for 24 hours.

To 45 ml of the above culture broth was added 4.5 ml of methanol containing 450 mg of a racemic methyl 3-(4-methylphenyl)glycidate, and further calcium chloride in an amount to the concentration of 1 mM in the reaction mixture and cetyltrimethylammonium bromide in an amount to 0.01% were added to carry out stereoselective hydrolysis at 30° C. for 72 hours. After the reaction, the mixture was extracted with addition of 45 ml of toluene, and the content of the content of methyl (2S, 3R)-3-(4-methylphenyl)glycidate was measured. As the result, the content of the (2S, 3R) isomer in the reaction mixture was as shown below in Table 5, and substantially no (2R, 3S) isomer which is the antipode thereof was detected in the reaction mixture.

TABLE 5

| Microorganism employed | (2S, 3R) isomer content (mg/ml) |
| --- | --- |
| Achromobacter dentriticum OUT 8009 | 0.8 |
| Achromobacter liquidium OUT 8012 | 0.8 |
| Agrobacterium, radiobacter IAM 1526 | 3.0 |
| Bacillus subtilis OUT 8234 | 0.8 |
| Brevibacterium helvolum IAM 1637 | 2.4 |
| Brevibacterium imperiale IAM 1654 | 1.6 |
| Citrobacter freundii ATCC 8090 | 2.4 |
| Flavobacterium sp. FERP-P No. 6901 | 1.1 |
| Micrococcus ureae IAM 1010 | 3.4 |
| Pseudomonas dacunhae IAM 1199 | 2.0 |
| Pseudomonas fluorescent IAM 1219 | 2.2 |
| Pseudomonas fluorescent IAM 1236 | 2.4 |
| Pseudomonas taetrolens IFO 3460 | 2.5 |
| Pseudomonas ovalis IAM 1002 | 1.5 |
| Pseudomonas ovalis IAM 1177 | 1.9 |
| Pseudomonas putida IAM 1512 | 2.6 |
| Pseudomonas putida FERP-P No. 3505 | 2.2 |
| Xanthomonas campestris IAM 1671 | 3.2 |

EXAMPLE 8

An amount 50 ml of a medium (pH 6.2) containing 1% of glucose, 0.5% of peptone, 0.3% of yeast extract, 0.3% of malt extract, 0.03% of a polyalkylene glycol derivative series surfactant (trade name: Karalin, available from Sanyo Kasei Kogyo K.K.), 0.1% of a polyoxyethylene derivative series surfactant (trade name: Tween 80, available from Atlas Powder Co., USA) was charged into a 500 ml volume shaking flask, and sterilized at 120° C. for 10 minutes. Into the medium was inoculated a mold or yeast shown below in Table 6, and subjected to shaking culture at 27° C. for 72 hours for the mold, and for 48 hours for the yeast. By use of 45 ml of the above culture broth, the reaction was carried out in the same manner as in Example 7 and the content of methyl (2S, 3R)-3-(4-methylphenyl)glycidate was measured. As the result, the content of the (2S, 3R) isomer in the reaction was as shown below in Table 6, and substantially no (2R, 3S) isomer which is the antipole thereof was detected in the reaction mixture.

TABLE 6

| Microorganism employed | (2S, 3R) isomer content (mg/ml) |
| --- | --- |
| Absidia glauca var. | 1.0 |

TABLE 6-continued

| Microorganism employed | (2S, 3R) isomer content (mg/ml) |
| --- | --- |
| paradoxa IFO 4007 | |
| Asperigillus flavus IFO 5839 | 1.6 |
| Asperigillus oryzae IFO 5710 | 2.3 |
| Candida guilliermondii IFO 0566 | 1.4 |
| Candida utilis IFO 0626 | 1.0 |
| Candida utilis IFO 1086 | 0.8 |
| Hansenula saturnus HUT 7087 | 0.8 |
| Kloeckera corticis IFO 0633 | 1.0 |
| Rhodotorula minuta OUT 6153 | 1.6 |
| Rhodotorula rubra OUT 6158 | 2.4 |
| Torulaspora delbrueckii IFO 0422 | 1.5 |
| Saccharomycopsis capsularis IFO 0672 | 1.4 |
| Torula utilis HUT 7526 | 1.9 |
| Candida saitoana IFO 0768 | 1.0 |
| Candida glabrata IFO 0005 | 1.6 |
| Torigonopsis variabilis IFO 0671 | 0.9 |

We claim:

1. A process for preparing an optically active (2S, 3R)-3-(4-methylphenyl)glycidic acid ester compound which comprises (a) permitting a culture broth, cells or treated cells of a microorganism having the ability of stereoselectivity hydrolyzing a (2R, 3S)-3-(4-methylphenyl)glycidic acid ester compound to act on a racemic trans-3-(4-methylphenyl)glycidic acid ester compound represented by the formula:

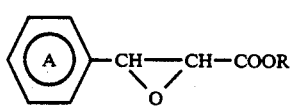

(I)

wherein Ring A is a 4-methylphenyl group, and R is an ester residue, thereby stereoselectively hydrolyzing the (2R, 3S) optically active isomer; and then (b) separating and collecting the (2S, 3R)-3-(4-methylphenyl)glycidic acid ester compound from the reaction mixture.

2. The process according to claim 1, wherein the microorganism is a microorganism belonging to the genus Micrococcus, the genus Achromobacter, the genus Agrobacterium, the genus Corynebacterium, the genus Enterobacter, the genus Flavobacterium, the genus Microbacterium, the genus Pseudomonas, the genus Rhizobium, the genus Sarcina, the genus Bacillus, the genus Brevibacterium, the genus Citrobacter, the genus Xanthomonas, the genus Candida, the genus Debaryomyces, the genus Hanseiaspora, the genus Hansenula, the genus Pichia, the genus Rhodosporidium, the genus Schizosaccharomyces, the genus Sporobolomyces, the genus Torula, the genus Kloeckera, the genus Rhodotorula, the genus Sacchamomycopsis, the genus Torulapsora, the genus Trigonopsis, the genus Absidia, the genus Aspergillus or the genus Streptomyces.

3. The process according to claim 1, wherein the compound to be separated and collected is a lower alkyl (2S, 3R)-3(4-methylphenyl)glycidate.

4. The process according to claim 1, wherein the compound to be separated and collected is methyl (2S, 3R)-3-(4ethylphenyl)glycidate.

5. The process according to claim 1, wherein the stereoselective hydrolysis reaction is practiced by contacting the microorganism with a racemic trans-3(4-methylphenyl)glycidic acid ester compound in a solvent.

6. The process according to claim 5, wherein the reaction is practiced with a substrate concentration of 0.1 to 80% at a temperature of 10° to 50° C. and a pH of 4 to 9.

7. A process for preparing (−)-cis-2-(4′-methylphenyl)-3-acetyloxy-5-(2-(dimethylamino)ethyl)-8-methyl-2,2-dihydro -1,5-benzothiazepin-4(5H)-one, which comprises (a) permitting a culture broth, cells or treated cells of a microorganism having the ability of stereoselectively hydroglyzing a (2R, 3S)-3-(4-methylphenyl)glycidic acid ester compound to act on a racemic trans-3-(4-methylphenyl)glycidic acid ester compound represented by the formula:

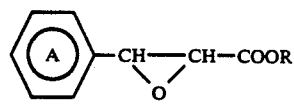

(I)

wherein Ring A is a 4-methylphenyl group, and R is an ester residue, thereby hydrolyzing the (2R, 3S) optically active isomer;

(b) separating and collecting the (2S, 3R) antipode from the reaction mixture; and then (c) converting said compound to (−)-cis-2-(4′-methylphenyl) -3-acetyloxy-5-(2-(dimethylamino)ethyl)-8-methyl-2,3-dihydro-1,5-benzothiazepin-4(5H)-one.

8. The process according to claim 7, wherein the microorganism is a microorganism belonging to the genus Micrococcus, the genus Achromobacter, the genus Agrobacterium, the genus Corynebacterium, the genus Enterobacter, the genus Flavobacterium, the genus Microbacterium, the genus Pseudomonas, the genus Rhizobium, the genus Sarcina, the genus Bacillus, the genus Brevibacterium, the genus Citrobacter, the genus Xanthomonas, the genus Candida, the genus Debaryomyces, the genus Hanseiaspora, the genus Hansenula, the genus Pichia, the genus Rhodosporidium, the genus Schizosaccharomyces, the genus Sporobolomyces, the genus Torula, the genus Kloeckera, the genus Rhodotorula, the genus Sacchamomycopsis, the genus Torulapsora, the genus Trigonopsis, the genus Absidia, the genus Aspergillus or the genus Streptomyces.

* * * * *